US00RE47526E

(19) United States
(12) Reissued Patent
Dunkley et al.

(10) Patent Number: US RE47,526 E
(45) Date of Reissued Patent: *Jul. 23, 2019

(54) AEROSOLIZATION APPARATUS WITH AIR INLET SHIELD

(71) Applicant: Novartis AG, Basel (CH)

(72) Inventors: Michael John Dunkley, Nottingham (GB); Jon David Tuckwell, Cambridgeshire (GB); Edward William Vernon-Harcourt, Cambridge (GB); Sameer Shirgaonkar, London (GB)

(73) Assignee: BGP Products, Allschwil (CH)

( * ) Notice: This patent is subject to a terminal disclaimer.

(21) Appl. No.: 14/098,403

(22) Filed: Dec. 5, 2013

Related U.S. Patent Documents

Reissue of:
(64) Patent No.: 8,069,851
Issued: Dec. 6, 2011
Appl. No.: 12/456,807
Filed: Jun. 22, 2009

U.S. Applications:
(63) Continuation of application No. 10/822,850, filed on Apr. 9, 2004, now Pat. No. 7,559,325.

(60) Provisional application No. 60/461,679, filed on Apr. 9, 2003.

(51) Int. Cl.
*A61M 11/00* (2006.01)
*A61M 15/00* (2006.01)

(52) U.S. Cl.
CPC ..... *A61M 15/0028* (2013.01); *A61M 15/003* (2014.02); *A61M 15/0033* (2014.02); *A61M 2202/064* (2013.01); *A61M 2206/16* (2013.01)

(58) Field of Classification Search
USPC ..... 128/863, 203.15, 203.21
See application file for complete search history.

(56) References Cited

U.S. PATENT DOCUMENTS

| | | | |
|---|---|---|---|
| 3,012,694 | A | 12/1961 | Johnston |
| 3,809,084 | A | 5/1974 | Hansen |
| 3,888,253 | A | 6/1975 | Watt et al. |

(Continued)

FOREIGN PATENT DOCUMENTS

| | | |
|---|---|---|
| EP | 0839544 | 5/1998 |
| EP | 1068874 | 1/2001 |

(Continued)

OTHER PUBLICATIONS

International Search Report, PCT/US2004/019028 (Sep. 8, 2004).
Tuckwell Jon et al "Aerosolization Apparatus with Capsule Puncturing Member" U.S. Appl. 10/821,652 (Apr. 9, 2003).

*Primary Examiner* — Joseph A Kaufman

(57) ABSTRACT

An aerosolization apparatus comprises a housing defining a chamber having a plurality of air inlets. The chamber contains an aerosolizable pharmaceutical formulation or is sized to receive a receptacle which contains an aerosolizable pharmaceutical formulation. A shield covers at least one of the air inlets or a portion of at least one of the air inlets. The shield prevents blockage of the air inlet by a user grasping the apparatus and inadvertently covering the air inlet. An end section is associated with the housing. The end section is sized and shaped to be received in a user's mouth or nose so that the user may inhale through the end section to inhale aerosolized pharmaceutical formulation that has exited the receptacle.

21 Claims, 4 Drawing Sheets

(56) References Cited

U.S. PATENT DOCUMENTS

| | | | | |
|---|---|---|---|---|
| 3,906,950 | A | 9/1975 | Cocozza | |
| 3,918,451 | A * | 11/1975 | Steil | 128/203.21 |
| 3,991,761 | A | 11/1976 | Cocozza | |
| 4,069,819 | A | 1/1978 | Valentini et al. | |
| 4,114,615 | A | 9/1978 | Wetterlin | |
| 4,116,195 | A | 9/1978 | James | |
| 4,247,066 | A | 1/1981 | Frost et al. | |
| 4,265,236 | A | 5/1981 | Pacella | |
| 4,338,931 | A | 7/1982 | Cavazza | |
| 4,846,876 | A | 7/1989 | Draber et al. | |
| 4,884,565 | A | 12/1989 | Cocozza | |
| 4,889,114 | A | 12/1989 | Kladders | |
| 4,995,385 | A | 2/1991 | Valentini et al. | |
| 5,152,284 | A | 10/1992 | Valentini et al. | |
| 5,201,308 | A | 4/1993 | Newhouse | |
| 5,263,475 | A | 11/1993 | Altermatt et al. | |
| 5,287,850 | A | 2/1994 | Haber et al. | |
| 5,301,666 | A | 4/1994 | Lerk et al. | |
| 5,379,763 | A | 1/1995 | Martin | |
| 5,458,135 | A | 10/1995 | Patton et al. | |
| 5,619,985 | A * | 4/1997 | Ohki et al. | 128/203.21 |
| 5,715,811 | A | 2/1998 | Ohki et al. | |
| 5,775,320 | A | 7/1998 | Patton et al. | |
| 5,785,049 | A | 7/1998 | Smith et al. | |
| 5,874,064 | A | 2/1999 | Edwards et al. | |
| 5,881,719 | A * | 3/1999 | Gottenauer et al. | 128/203.15 |
| 5,894,841 | A | 4/1999 | Voges | |
| 5,921,236 | A | 7/1999 | Ohki et al. | |
| 5,922,675 | A | 7/1999 | Baker et al. | |
| 5,985,309 | A | 11/1999 | Edwards et al. | |
| 5,992,675 | A | 11/1999 | Kerr | |
| 6,089,228 | A | 7/2000 | Smith et al. | |
| 6,138,668 | A | 10/2000 | Patton et al. | |
| 6,186,141 | B1 | 2/2001 | Pike et al. | |
| 6,230,707 | B1 | 5/2001 | Hörlin | |
| 6,257,233 | B1 | 7/2001 | Burr et al. | |
| 6,357,490 | B1 | 3/2002 | Johnston et al. | |
| 6,418,926 | B1 | 7/2002 | Chawla | |
| 6,503,480 | B1 | 1/2003 | Edwards et al. | |
| 6,520,179 | B1 | 2/2003 | Schuckmann et al. | |
| 6,546,929 | B2 | 4/2003 | Burr et al. | |
| 6,655,379 | B2 | 12/2003 | Clark et al. | |
| 6,679,256 | B2 | 1/2004 | Ingle et al. | |
| 6,681,767 | B1 | 1/2004 | Patton et al. | |
| 6,705,313 | B2 | 3/2004 | Niccolai | |
| 6,715,486 | B2 | 4/2004 | Gieschen et al. | |
| 6,732,732 | B2 | 5/2004 | Edwards et al. | |
| 6,766,799 | B2 | 7/2004 | Edwards et al. | |
| 6,901,929 | B2 | 6/2005 | Burr et al. | |
| 6,907,880 | B1 | 6/2005 | Heckenmüller et al. | |
| 6,948,496 | B2 | 9/2005 | Eason et al. | |
| 7,185,651 | B2 | 3/2007 | Alston et al. | |
| 7,271,156 | B2 * | 9/2007 | Krieg et al. | 514/44 A |
| 7,278,425 | B2 | 10/2007 | Edwards et al. | |
| 7,481,212 | B2 | 1/2009 | Schuler et al. | |
| 7,540,284 | B2 * | 6/2009 | Patton et al. | 128/203.12 |
| 7,559,325 | B2 * | 7/2009 | Dunkley et al. | 128/203.21 |
| 7,905,230 | B2 | 3/2011 | Schuler et al. | |
| 2002/0000225 | A1 | 1/2002 | Schuler et al. | |
| 2003/0094173 | A1 | 5/2003 | Burr et al. | |
| 2003/0131847 | A1 | 7/2003 | Niccolai | |
| 2003/0150454 | A1 | 8/2003 | Burr et al. | |
| 2003/0168057 | A1 | 9/2003 | Snyder et al. | |
| 2003/0183229 | A1 | 10/2003 | Smith et al. | |
| 2004/0206350 | A1 | 10/2004 | Alston et al. | |
| 2005/0000518 | A1 | 1/2005 | Dunkley et al. | |
| 2005/0022812 | A1 | 2/2005 | Hrkach | |
| 2005/0022813 | A1 | 2/2005 | Alston | |
| 2005/0051162 | A1 | 3/2005 | Schuler et al. | |
| 2005/0051166 | A1 | 3/2005 | Glusker et al. | |
| 2005/0056276 | A1 | 3/2005 | Schuler et al. | |
| 2005/0056280 | A1 | 3/2005 | Alston et al. | |
| 2005/0081852 | A1 | 4/2005 | Rangachari | |
| 2005/0090798 | A1 | 4/2005 | Clark et al. | |
| 2005/0092323 | A1 | 5/2005 | Frietsch et al. | |
| 2005/0150492 | A1 | 7/2005 | Dunkley et al. | |
| 2006/0254583 | A1 | 11/2006 | Deboeck et al. | |

FOREIGN PATENT DOCUMENTS

| | | |
|---|---|---|
| EP | 1329236 | 7/2003 |
| WO | WO-95/24183 | 9/1995 |
| WO | WO-96/32096 | 10/1996 |
| WO | WO-96/32149 | 10/1996 |
| WO | WO-99/16419 | 4/1999 |
| WO | WO-99/16422 | 4/1999 |
| WO | WO-00/07572 | 2/2000 |
| WO | WO-00/72904 | 12/2000 |
| WO | WO-01/70318 | 9/2001 |
| WO | WO-02/11802 | 2/2002 |
| WO | WO-02/83220 | 10/2002 |
| WO | WO 02083220 | 10/2002 |
| WO | WO-2009/75794 | 6/2009 |
| WO | WO 20009075794 | 6/2009 |

* cited by examiner

FIG. 4
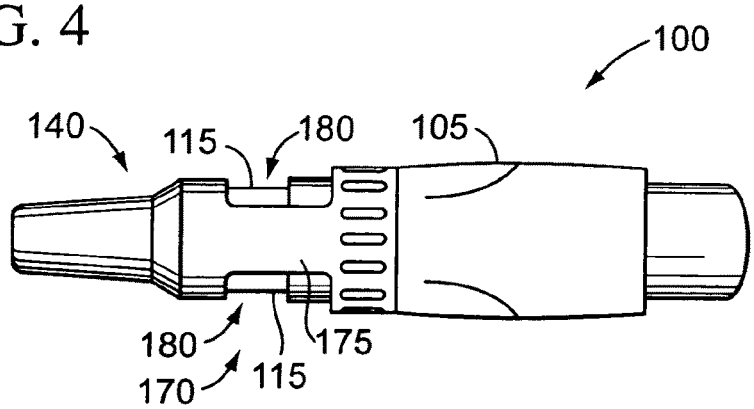
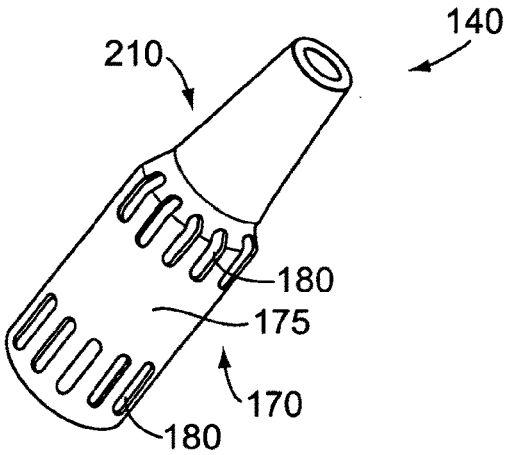
FIG. 5
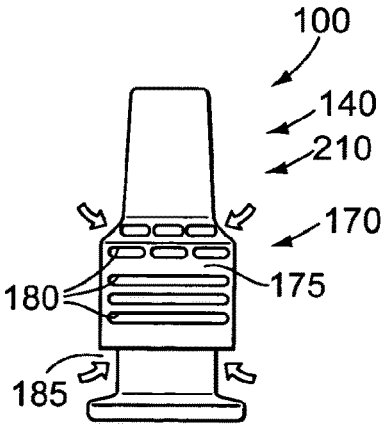
FIG. 6
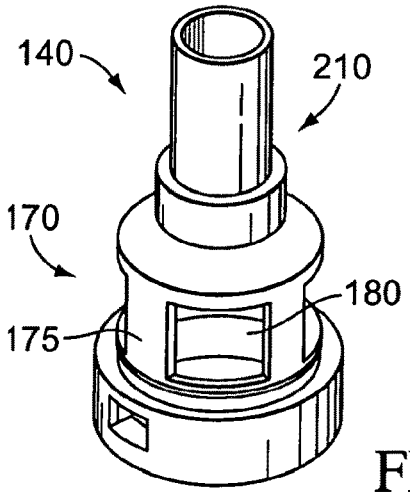
FIG. 7

AEROSOLIZATION APPARATUS WITH AIR INLET SHIELD

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This is a continuation of application Ser. No. 10/822,850 filed on Apr. 9, 2004, which claims the benefit of U.S. Provisional Application No. 60/461,679 filed Apr. 9, 2003, the entire disclosures of which are hereby incorporated by reference.

This application claims the benefit U.S. Provisional Patent Application Ser. No. 60/461,679 filed on Apr. 9, 2003, which is incorporated herein by reference in its entirety.

BACKGROUND

The need for effective therapeutic treatment of patients has resulted in the development of a variety of techniques for delivering a pharmaceutical formulation to a patient. One traditional technique involves the oral delivery of a pharmaceutical formulation in the form of a pill, capsule, or the like. Inhaleable drug delivery, where an aerosolized pharmaceutical formulation is orally or nasally inhaled by a patient to deliver the formulation to the patient's respiratory tract, has also proven to be an effective manner of delivery. In one inhalation technique, a pharmaceutical formulation is delivered deep within a patient's lungs where it may be absorbed into the blood stream. In another inhalation technique, a pharmaceutical formulation is delivered locally to a particular site, such as an infected lung. Many types of inhalation devices exist including devices that aerosolize a dry powder pharmaceutical formulation.

One type of inhalation device aerosolizes a pharmaceutical formulation that is stored in a capsule. For example, a dose or a portion of a dose of a dry powder pharmaceutical formulation may be stored in a capsule, and the capsule may be inserted into an aerosolization device which is capable of aerosolizing the pharmaceutical formulation. The aerosolization may be accomplished by causing the capsule to move within a chamber, for example by flowing air through the chamber using a user's inhalation pressure to generate the airflow. As the capsule moves within the chamber, the pharmaceutical formulation exits the capsule though one or more openings in the capsule, and the pharmaceutical formulation is entrained by the flowing air in an aerosolized form. The aerosolized pharmaceutical formulation may then be inhaled by the user, and a dose or portion of a dose of the aerosolized pharmaceutical formulation may be delivered to the user's respiratory tract.

The size and quality of the dose delivered to the user is dependent on the amount and condition of aerosolizable pharmaceutical formulation that exits the capsule. However, in conventional aerosolization devices, the amount and condition of the aerosolizable pharmaceutical formulation may vary from use to use and/or from user to user. For example, sometimes it is difficult to cause large amounts of the pharmaceutical formulation to exit the capsule when a user is unable to generate a high flow rate of air through the device. The inefficient release of pharmaceutical formulation can be costly and can result in the necessity for numerous operations of the device in order to achieve a desire dosage. In some circumstances, the pharmaceutical formulation exits the capsule in agglomerated form, the agglomerations being undesirably large for inhalation therapy.

Therefore, it is desirable to be able to aerosolize a pharmaceutical formulation in a consistent manner. It is further desirable to be able to aerosolize a pharmaceutical formulation in a manner that extracts an increased amount of the pharmaceutical formulation from a receptacle. It is also desirable to be able to aerosolize a pharmaceutical formulation in a more deagglomerated form.

SUMMARY

The present invention satisfies these needs. In one aspect of the invention, an aerosolization apparatus comprises a chamber that receives a receptacle, the chamber having a plurality of air inlets wherein at least one, but preferably not all, of the air inlets is shielded by a shielding member.

In another aspect of the invention, a handheld aerosolization apparatus comprises a housing defining a chamber having a plurality of air inlets, the chamber being sized to receive a receptacle which contains an aerosolizable pharmaceutical formulation; a shield which covers at least one but not all of the air inlets, whereby the shield prevents blockage of the at least one air inlet by a user grasping the apparatus; and an end section associated with the housing, the end section sized and shaped to be received in a user's mouth or nose so that the user may inhale through the end section to inhale aerosolized pharmaceutical formulation that has exited the receptacle.

In another aspect of the invention, a handheld aerosolization apparatus comprises a housing defining a chamber having a plurality of air inlets, the chamber being sized to receive a receptacle which contains an aerosolizable pharmaceutical formulation; a shield which covers a portion of but not all of at least one of the air inlets; and an end section associated with the housing, the end section sized and shaped to be received in a user's mouth or nose so that the user may inhale through the end section to inhale aerosolized pharmaceutical formulation that has exited the receptacle.

In another aspect of the invention, a handheld aerosolization apparatus comprises a housing defining a chamber having one or more air inlets, the chamber being sized to receive a receptacle which contains an aerosolizable pharmaceutical formulation; a shield extending around only a portion of transverse circumference of the housing, the shield covering at least one air inlets, whereby the shield prevents blockage of the at least one air inlet by a user grasping the apparatus; and an end section associated with the housing, the end section sized and shaped to be received in a user's mouth or nose so that the user may inhale through the end section to inhale aerosolized pharmaceutical formulation that has exited the receptacle.

In another aspect of the invention, a method of aerosolizing a pharmaceutical formulation comprises providing an aerosolizable pharmaceutical formulation in a chamber, the chamber having a plurality of air inlets; shielding at least one but not all of the air inlets from being blocked by a user grasping the chamber; aerosolizing the pharmaceutical formulation by flowing air through the chamber; and administering the aerosolized pharmaceutical formulation to the respiratory tract of a user during the user's inhalation.

In another aspect of the invention, a method of aerosolizing a pharmaceutical formulation comprises providing an aerosolizable pharmaceutical formulation in a chamber, the chamber having one or more air inlets; shielding only a portion of at least one of the air inlets from being blocked by a user grasping the chamber; aerosolizing the pharmaceutical formulation by flowing air through the chamber; and administering the aerosolized pharmaceutical formulation to the respiratory tract of a user during the user's inhalation.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

FIG. 4 is a schematic side view of a version of an aerosolization apparatus;

FIG. 5 is a schematic side view of a version of an inlet shield for use with an aerosolization apparatus;

FIG. 6 is a schematic side view of another version of an inlet shield for use with an aerosolization apparatus; and FIG. 7 is a schematic side view of another version of an inlet shield for use with an aerosolization apparatus.

DESCRIPTION

The present invention relates to an aerosolization apparatus. In particular, the invention relates to an aerosolization apparatus capable of aerosolizing a pharmaceutical formulation contained in a receptacle, such as a capsule. Although the process is illustrated in the context of aerosolizing a dry powder pharmaceutical formulation for inhalation, the present invention can be used in other processes and should not be limited to the examples provided herein.

Figure 1A:
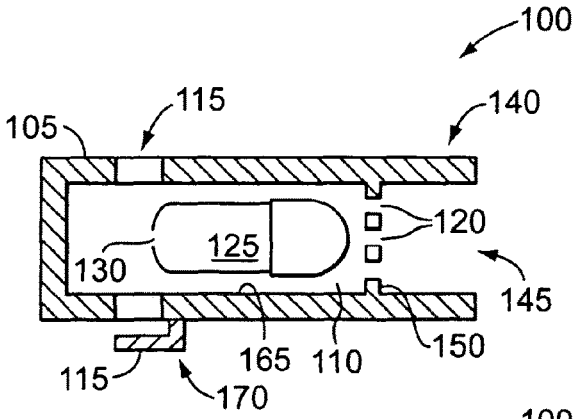
FIG. 1A is a schematic sectional side view of a version of an aerosolization apparatus according to the invention in an initial position.

An aerosolization apparatus 100 according to the present invention is shown schematically in FIG. 1A. The aerosolization apparatus 100 comprises a housing 105 defining a chamber 110 having one or more air inlets 115 and one or more air outlets 120. The chamber 110 is sized to receive a receptacle 125 which contains an aerosolizable pharmaceutical formulation. The receptacle 125 has an opening 130 thereinto that provides a communication between the chamber 110 and the pharmaceutical formulation within the receptacle 125. Near or adjacent the outlet 120 is an end section 140 that may be sized and shaped to be received in a user's mouth or nose so that the user may inhale through an opening 145 in the end section 140 that is in communication with the chamber outlet 120.

Figure 1B:
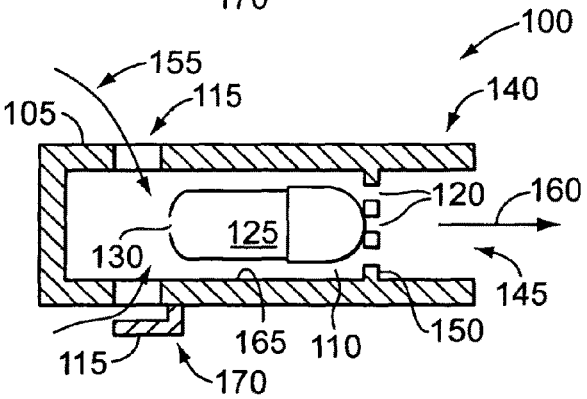
FIG. 1B is a schematic sectional side view of the version of an aerosolization apparatus shown in FIG. 1A at the beginning of an aerosolization process.
Figure 1C:
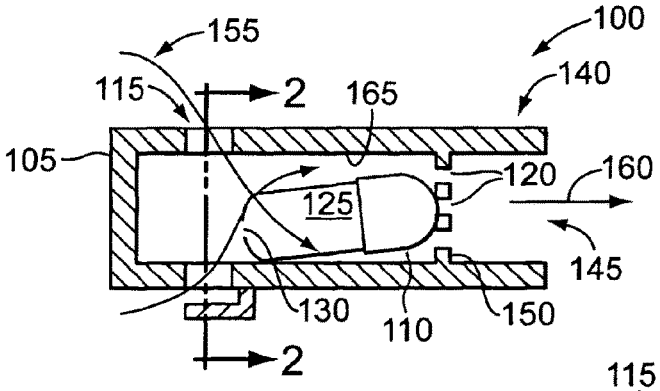
FIG. 1C is a schematic sectional side view of the version of an aerosolization apparatus shown in FIG. 1A during an aerosolization process.

The aerosolization apparatus 100 utilizes air flowing through the chamber 110 to aerosolize the pharmaceutical formulation in the receptacle 125. For example, FIGS. 1A through 1C illustrate the operation of a version of an aerosolization apparatus 100 where air flowing through the inlet 115 is used to cause aerosolization of the pharmaceutical formulation and the aerosolized pharmaceutical formulation flows through the outlet 120 so that it may be delivered to the user through the opening 145 in the end section 140. The aerosolization apparatus 100 is shown in its initial condition in FIG. 1A. The receptacle 125 is positioned within the chamber 110 and the pharmaceutical formulation is secured within the receptacle 125. In the version shown, a partition 150 blocks the forward end of the chamber 110, and the partition 150 has the one or more outlets 120 extending therethrough.

Air or other gas is then caused to flow through an inlet 115, as shown by arrows 155 in FIG. 1B. For example, the airflow 155 may be generated by a user inhaling 160 through the opening 145 in the end section 140. The airflow 155 initially draws the receptacle toward the partition 150. Continued airflow 155, as shown in FIG. 1C, causes the receptacle 125 to move within the chamber 110. In the configuration shown, the receptacle 125 may contact the partition 150 at its forward end and then move about the sidewall 165 of the capsule with its rearward end contacting the sidewall 165. For example, the rearward end of the receptacle 125 may rotate and/or slide around the sidewall 165 of the chamber 110. This movement causes the pharmaceutical formulation in the receptacle 125 to exit through the opening 130 and become aerosolized in the airflow 155. The aerosolized pharmaceutical formulation is then delivered to the user's respiratory tract during the user's inhalation 160. In another version, compressed air or other gas may be ejected into an inlet 115 to cause the aerosolizing air flow 155, and the aerosolized pharmaceutical formulation is then inhaled by the user.

Figure 2:
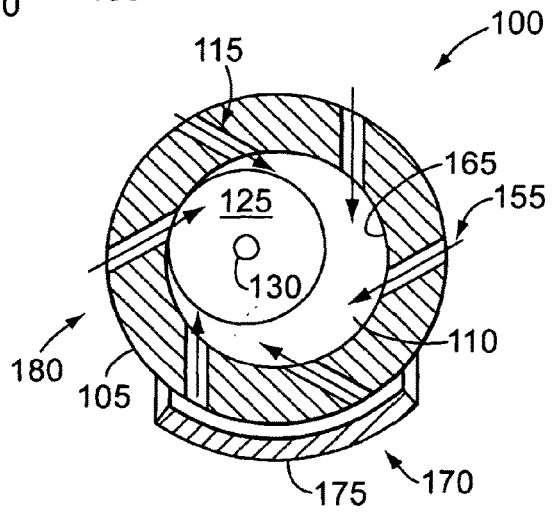
FIG. 2 is a schematic sectional end view of a version of an aerosolization apparatus having an air inlet shield.

The aerosolization apparatus 100 also comprises an air inlet shielding member 170. As shown in FIG. 1A, the air inlet shielding member 170 comprises a covering portion 175 that at least partially covers one or more of the inlets 115. The shielding member 170 prevents blockage of the air flow by preventing at least one of the inlets 115 from being blocked by a user's fingers or hand during use. Accordingly, if a user inadvertently grasps the apparatus in the area of the inlets 115, the user will the shielding member 170 rather than one or more of the inlets 115 and air will still flow through into the chamber 110. As can be seen in FIGS. 1B and 1C, the air flow 155 takes a more tortuous path in the region of the shielding member 170. Accordingly, in one version, it is preferred that the shielding member not cover all of the inlets 115 in that such coverage will increase the flow resistance within the apparatus. In another version, it is desirable to increase the flow resistance through the apparatus and coverage of all or a plurality of the inlets is desirable. The cross-section of a version of an aerosolization apparatus 100 is shown in FIG. 2. In this version, the shielding member 170 covers less than half of the inlets 115. In this configuration, adequate air flow through the device is assured independent of user finger positioning. By cover it is meant overlap in the radial or outward direction.

A version of an aerosolization apparatus 100 comprising a shielding member 170 is shown in FIGS. 3A through 3E. In this version, the housing 105 of the aerosolization apparatus 100 comprises a body 205 and a removable endpiece 210. The endpiece 210 may be removed from the body 205 to insert a receptacle 125 in the chamber 110 which is formed when the body 205 and the endpiece 210 are connected together. The endpiece 210 comprises a partition 150 that is dome-shaped 215 and that blocks the forward end of the chamber 110, and the partition 215 has the one or more outlets 120 extending therethrough. Examples of aerosolization apparatus with a partition 150 and chamber configuration are described in U.S. Pat. No. 4,069,819 and in U.S. Pat. No. 4,995,385, both of which are incorporated herein by reference in their entireties. The inlets 115 comprise a plurality of tangentially oriented slots 220. When a user inhales 160 through the endpiece 210, outside air is caused to flow through the tangential slots 220 as shown by arrows 225 in FIG. 3E. This airflow 225 creates a swirling airflow within the chamber 110. The swirling airflow causes the receptacle 125 to contact the partition 150 and then to move within the chamber 110 in a manner that causes the pharmaceutical formulation to exit the receptacle 125 and become entrained within the swirling airflow. In one specific version, the chamber 110 comprises a tapered section 230 that terminates at an edge 235. During the flow of swirling air in the chamber 110, the forward end of the receptacle 125 contacts and rests on the partition 150 and a sidewall of the receptacle 125 contacts the edge 235 and slides and/or rotates along the edge 235. This motion of the capsule is particularly effective in forcing a large amount of the pharmaceutical formulation through one or more openings 130 in the rear of the receptacle 125.

Figure 3A:
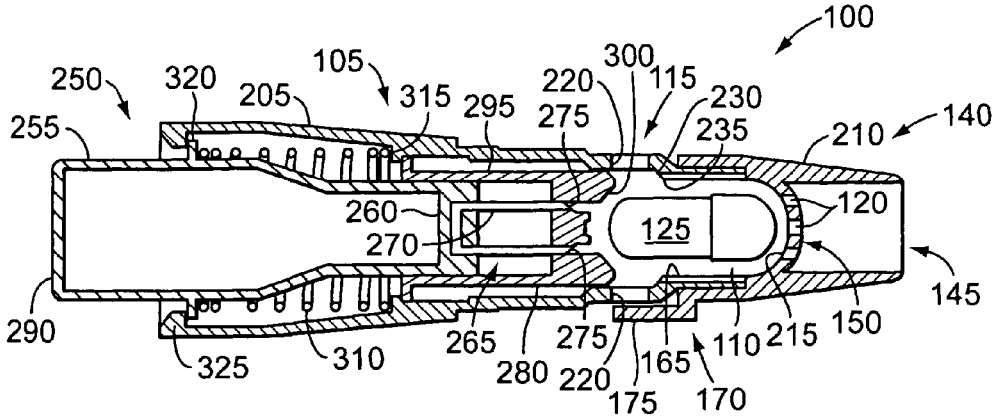
FIG. 3A is a schematic sectional side view of a version of an aerosolization apparatus in a rest position.
Figure 3B:
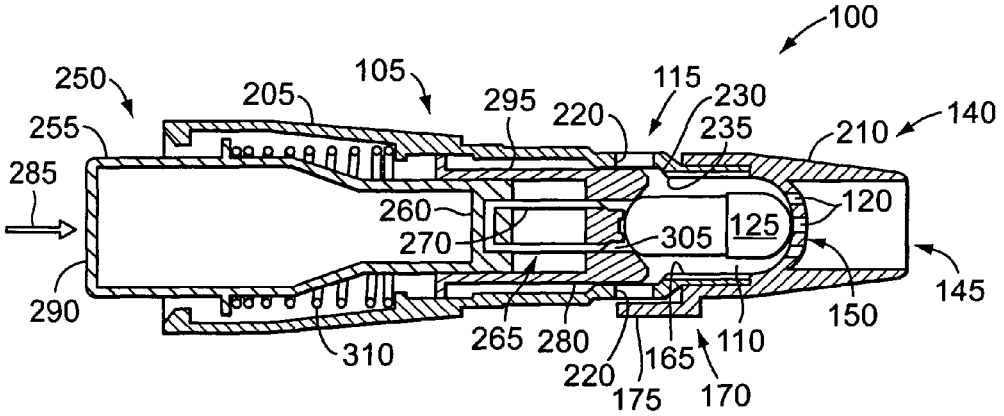
FIG. 3B is a schematic sectional side view of the version of an aerosolization apparatus shown in FIG. 3A just before capsule puncture.
Figure 3C:
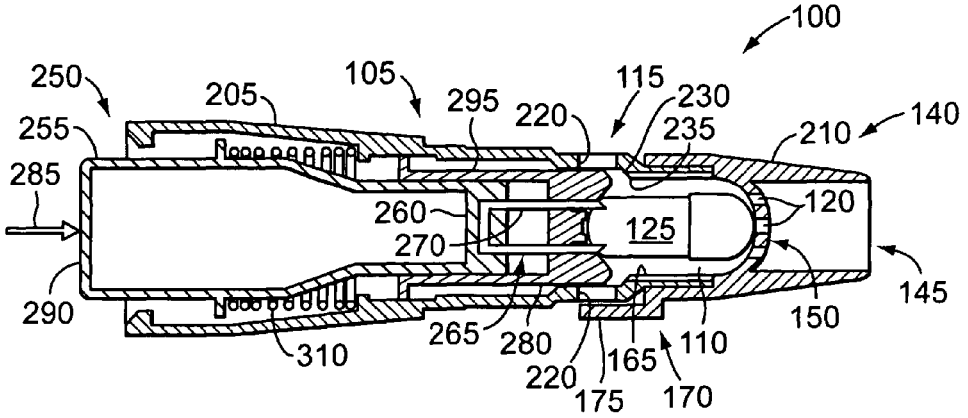
FIG. 3C is a schematic sectional side view of the version of an aerosolization apparatus shown in FIG. 3A as the capsule is being punctured.
Figure 3D:
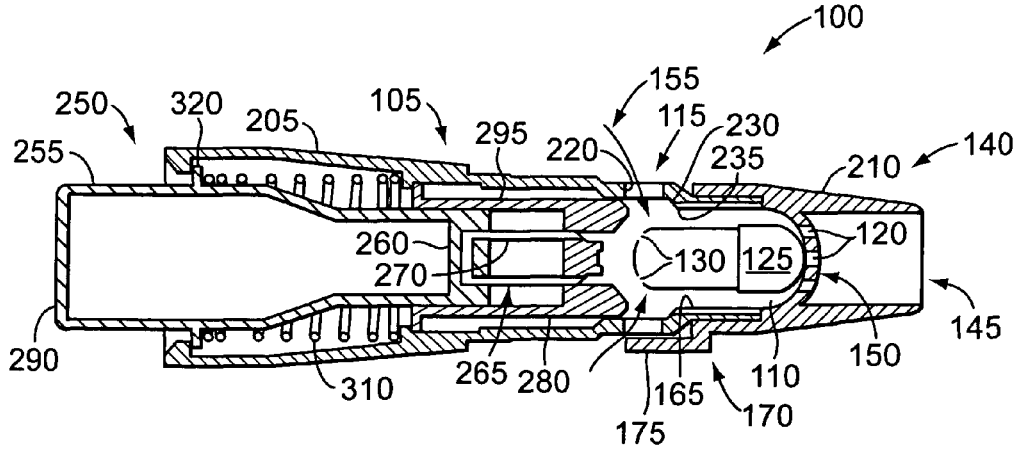
FIG. 3D is a schematic sectional side view of the version of an aerosolization apparatus shown in FIG. 3A just after capsule puncture.
Figure 3E:
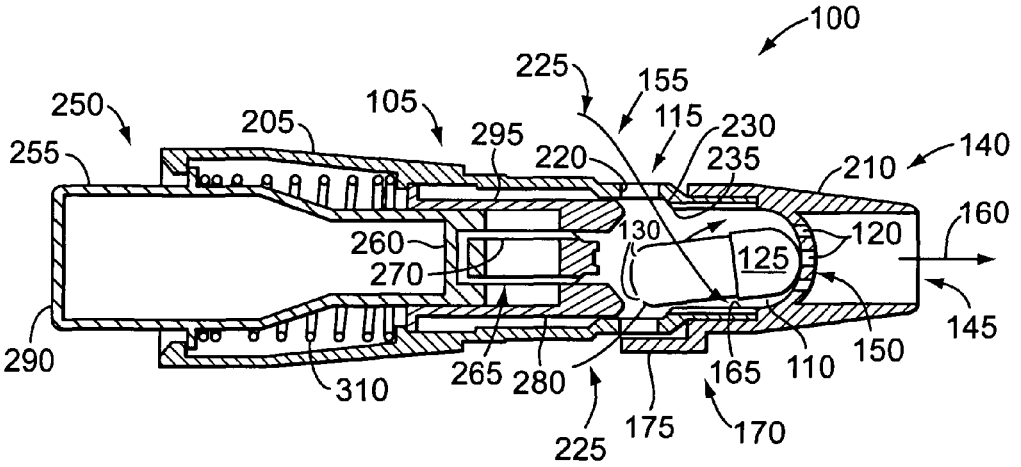
FIG. 3E is a schematic sectional side view of the version of an aerosolization apparatus shown in FIG. 3A in use.

The one or more openings 130 in the rear of the receptacle 125 in the version of FIGS. 3A through 3E are created by a puncturing mechanism 250 that is slidable within the body 205. The puncturing mechanism 250, shown in its rest position in FIG. 3A, comprises a plunger 255 attached at its forward end 260 to a puncture member 265, which in the version shown is a U-shaped staple 270 having two sharpened tips 275. The puncturing mechanism 250 further comprises a seating member 280 which contacts the plunger 255 and/or the puncture member 265 and is slidable relative to the plunger 255 and the puncture member 265. To create the openings 130 in the receptacle 125, the user applies a force 285 to the plunger 255, as shown in FIG. 3B, such as by pressing against an end surface 290 of the plunger 255 with the user's finger or thumb. The force 285 causes the plunger to slide within the body 205. A slight frictional contact between the plunger 255 the a rear section 295 of the seating member 280 causes the seating member 280 to also slide within the body 205 until a forward seating surface 300 of the seating member 280 contacts the receptacle 125, as shown in FIG. 3B. The forward seating surface 300, which may be shaped to generally match the shape of the receptacle 125, secures the receptacle 125 between the seating member 280 and the partition 150. The continued application of force 285 causes the plunger 255 and the puncture member 265 to slide relative to the seating member 280, as shown in FIG. 3C, to advance the puncture member 135 through openings 305 in the forward seating surface 300 and into the receptacle 125. Upon the removal of the force 285, a spring 310 or other biasing member urges the puncturing mechanism 250 back to its rest position. For example, the spring 310 may contact a shoulder 315 in the body 205 and press a flange 320 on the plunger 255 toward a rim 325 in the body 205. The frictional engagement between the plunger 355 and the seating member 280 also returns the seating member 280 to its retracted position when the plunger is returned to its retracted position.

In the version of FIGS. 3A through 3E, the shielding member 170 is an integral portion of the endpiece 210. Accordingly, in this version, if the user installs the endpiece 210 and then uses the aerosolization apparatus 100 without adjusting his or her grip on the endpiece 210, none of the inlets 220 will be covered by the user. The provision of the shielding member 170 on the endpiece 210 has additional advantages. For example, the shielding member 170 can serve to lengthen and/or widen the endpiece 210 thereby reducing the risk of a user choking on the endpiece 210 if the endpiece 210 were to become inadvertently disconnected from the body of the apparatus.

In one version, the receptacle 125 comprises a capsule. The capsule may be of a suitable shape, size, and material to contain the pharmaceutical formulation and to provide the pharmaceutical formulation in a usable condition. For example, the capsule may comprise a wall which comprises a material that does not adversely react with the pharmaceutical formulation. In addition, the wall may comprise a material that allows the capsule to be opened to allow the pharmaceutical formulation to be aerosolized. In one version, the wall comprises one or more of gelatin, hydroxypropyl methylcellulose (HPMC), polyethyleneglycol-compounded HPMC, hydroxyproplycellulose, agar, or the like. Alternatively or additionally, the capsule wall may comprise a polymeric material, such as polyvinyl chloride (PVC). In one version, the capsule may comprise telescopically ajoined sections, as described for example in U.S. Pat. No. 4,247,066 which is incorporated herein by reference in its entirety. The interior of the capsule may be filled with a suitable amount of the pharmaceutical formulation, and the size of the capsule may be selected to adequately contain a desired amount of the pharmaceutical formulation. The sizes generally range from size 5 to size 000 with the outer diameters ranging from about 4.91 mm to 9.97 mm, the heights ranging from about 11.10 mm to about 26.14 mm, and the volumes ranging from about 0.13 ml to about 1.37 ml, respectively. Suitable capsules are available commercially from, for example, Shionogi Qualicaps Co. in Nara, Japan and Capsugel in Greenwood, S.C. After filling, a top portion may be placed over the bottom portion to form the a capsule shape and to contain the powder within the capsule, as described in U.S. Pat. No. 4,846,876, U.S. Pat. No. 6,357,490, and in the PCT application WO 00/07572 published on Feb. 17, 2000, all of which are incorporated herein by reference in their entireties.

In another version, the aerosolization apparatus 100 may be configured differently than as shown in FIGS. 1A through 1C and 3A through 3E. For example, the chamber 100 may be sized and shaped to receive the receptacle 125 so that the receptacle 125 is orthogonal to the inhalation direction, as described in U.S. Pat. No. 3,991,761. As also described in U.S. Pat. No. 3,991,761, the puncturing mechanism 250 may puncture both ends of the receptacle 125. In such version, the non-circular cross-section may be provided along a sidewall that contacts the ends of the capsule. In another version, the chamber may receive the receptacle in a manner where air flows through the receptacle as described for example in U.S. Pat. No. 4,338,931 and in U.S. Pat. No. 5,619,985. In another version, the aerosolization of the pharmaceutical formulation may be accomplished by pressurized gas flowing through the inlets, as described for example in U.S. Pat. No. 5,458,135, U.S. Pat. No. 5,785,049, and U.S. Pat. No. 6,257,233, or propellant, as described in PCT Publication WO 00/72904 and U.S. Pat. No. 4,114,615. All of the above references being incorporated herein by reference in their entireties.

A version of an aerosolization apparatus 100 having an endpiece 210 comprising an air inlet shielding member 170 is shown in FIG. 4. In this version, the shielding member 170 comprises two covering portions 175 (only one shown in the view of FIG. 4) and two open portions 180 between the diametrically opposed covering portions 175. Alternatively, there could be three, four, or more covering portions 175 separated by open portions 180. In the version shown, the user would grasp the apparatus by contacting the covering portions 175 and would therefore not block the air inlets 115. In one version, space would be provided between the covering portion 175 and the outer surface of the inlets 115 under the covering portion 175 in order to create a manifold airflow portion below the covering portion 175.

Other versions of an endpiece 210 which comprises a shielding member 170 are shown in FIGS. 5, 6, and 7. These versions show different arrangements for the covering portions 175 and the open portions 180 associated with the shielding member 170. In the version of FIG. 5 a series of longitudinal open portions 180 is provided. In the version of FIG. 6, one or more circumferentially extending open portions 180 are provided. In the version of FIG. 6, an open portion is also provided that extends circumferentially around the base 185 of and under the endpiece 210. While such open portion at the base 185 may be used in combination with one or more additional open portions 180, it has been discovered that it may be disadvantageous to provide the open portion at the base 185 as the only open portion 180. A user can easily occlude all or a portion of an open portion at the base 185 which can lead to inconsistent air flow through the device. In addition, air flowing through an open portion at the base 185 can encourage endpiece disconnection from the body.

In a preferred version, the invention provides a system and method for aerosolizing a pharmaceutical formulation and delivering the pharmaceutical formulation to the respiratory tract of the user, and in particular to the lungs of the user. The pharmaceutical formulation may comprise powdered medicaments, liquid solutions or suspensions, and the like, and may include an active agent.

The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including. without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFTR) gene, deoxyreibonuclease (Dnase), bactericidal/ permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof. Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperatures (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), both of which are incorporated herein by reference in their entireties.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered formulation for use in the present invention includes a dry powder having a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders may be greater than 30%, more preferably greater than 40%, more preferably greater than 50% and most preferably greater than 60% and the aerosol particle size distribution is about 1.0-5.0 μm mass median aerodynamic diameter (MMAD), usually 1.5-4.5 am MMAD and preferably 1.5-4.0 μm MMAD. These dry powders have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. [A handheld ] *An* aerosolization apparatus comprising:

a housing having [at least two ] air inlets, the inlets configured [and dimensioned ] to produce a swirling airflow;

an endpiece comprising a [perforated member and an aerosolized pharmaceutical formulation outlet] *partition having one or more outlets*, the endpiece being connectable to the housing to define a chamber, the chamber being sized to receive a capsule which contains an aerosolizable pharmaceutical formulation, the endpiece further comprising a shield which covers at least [one air inlet] *two but not all of the air inlets*, wherein the shield comprises at least one covering portion, whereby the covering portion prevents blockage of at least one air inlet by a user grasping the apparatus; and a puncturing mechanism disposed within the housing for creating one or more openings in *only one end of* the capsule, the puncturing mechanism comprising [an alignment guide ] *a seating member* and a puncture member, wherein the [alignment guide] *seating member* comprises a surface which advances to contact and [align ] *secure* the capsule *between the seating member and the partition* while the [alignment guide and ] puncture member [are ] *is* advanced into the capsule to create an opening in the capsule[, and wherein the surface comprises one or more protrusions for contacting the capsule].

2. An apparatus according to claim 1 wherein the shield comprises at least two covering portions intermediate to two open portions.

3. An apparatus according to claim 1 wherein the shield comprises at least four covering portions intermediate to at least four open portions.

4. An apparatus according to claim 1 wherein the shield covering portions [and open portions ] are displaced from said air inlets.

5. An apparatus according to claim 1 wherein the endpiece is removably connected to the housing and wherein the endpiece may be removed from the housing to provide access to the chamber.

6. An apparatus according to claim 1 wherein the shield extends longitudinally along the apparatus.

7. An apparatus according to claim 1 wherein the shield extends transversely along the apparatus.

8. An apparatus according to claim 1 wherein the chamber is elongated and wherein the capsule [is ] *may be* received lengthwise within the elongated chamber.

*9. An apparatus according to claim 1 in combination with the capsule wherein the capsule contains an aerosolizable pharmaceutical formulation comprising an active agent.*

*10. An apparatus according to claim 9 wherein the active agent comprises tobramycin.*

*11. An apparatus according to claim 9 wherein the active agent comprises ciprofloxacin.*

*12. An apparatus according to claim 9 wherein the active agent comprises amphotericin B.*

*13. An apparatus according to claim 9 wherein the active agent comprises an anti-infective.*

*14. An apparatus according to claim 9 wherein the active agent comprises an anti-asthma agent.*

*15. An apparatus according to claim 9 wherein the active agent comprises a bronchodilator.*

*16. An aerosolization apparatus comprising:*

*a housing having air inlets;*

*an endpiece comprising a partition having one or more outlets, the endpiece being connectable to the housing to define a chamber, the chamber being sized to receive a capsule which contains an aerosolizable pharmaceutical formulation, the endpiece further comprising a shield which covers at least two but not all of the air inlets, wherein the shield prevents blockage of at least one air inlet by a user grasping the apparatus; and*

*a puncturing mechanism disposed within the housing for creating one or more openings in only one end of the capsule,*

*wherein the endpiece is sized and shaped to be received in a user's mouth or nose so that the user may inhale through the end section to aerosolize the pharmaceutical formulation.*

*17. An apparatus according to claim 16 wherein the shield comprises at least two covering portions intermediate to two open portions.*

*18. An apparatus according to claim 16 wherein the shield comprises at least four covering portions intermediate to four open portions.*

*19. An apparatus according to claim 16 wherein the inlets are configured to produce a swirling airflow.*

*20. An apparatus according to claim 16 in combination with the capsule wherein the capsule contains an aerosolizable pharmaceutical formulation comprising tobramycin.*

*21. An apparatus according to claim 16 in combination with the capsule wherein the capsule contains an aerosolizable pharmaceutical formulation comprising ciprofloxacin.*

* * * * *